(12) United States Patent
Hughes

(10) Patent No.: US 7,470,545 B2
(45) Date of Patent: Dec. 30, 2008

(54) BUCCAL DISSOLUTION OF ACTIVE SUBSTANCES

(75) Inventor: Lyn Hughes, Harleysville, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 10/007,140

(22) Filed: Nov. 5, 2001

(65) Prior Publication Data

US 2003/0087457 A1 May 8, 2003

(51) Int. Cl.
G01N 1/28 (2006.01)
G01N 1/38 (2006.01)

(52) U.S. Cl. .................. 436/177; 73/866; 422/101; 436/164; 436/178

(58) Field of Classification Search ............. 422/68.1, 422/82.05, 101; 436/164, 177, 178, 181; 73/866

See application file for complete search history.

(56) References Cited

U.S. PATENT DOCUMENTS

| | | | | |
|---|---|---|---|---|
| 3,620,675 A | * | 11/1971 | Olson | 436/2 |
| 3,801,280 A | * | 4/1974 | Shah et al. | 436/2 |
| 4,279,860 A | * | 7/1981 | Smolen | 422/63 |
| 4,578,244 A | * | 3/1986 | Cosgrove et al. | 422/65 |
| 4,594,902 A | * | 6/1986 | Compton et al. | 73/863.23 |
| 5,127,278 A | * | 7/1992 | Benz | 73/866 |
| 5,142,920 A | * | 9/1992 | Bart et al. | 73/866 |
| 6,004,822 A | * | 12/1999 | Li et al. | 436/177 |
| 6,558,957 B1 | | 5/2003 | Roinestad et al. | |
| 6,799,123 B2 | * | 9/2004 | Hughes | 702/25 |

FOREIGN PATENT DOCUMENTS

JP  2000-283977 A  10/2000
JP  283977/2000  10/2000

OTHER PUBLICATIONS

Wong, et. al., "Formulation and evaluation of controlled release Eudragit buccal patches," Internat'l Journ. of Pharmaceutics, 1991, pp. 11-22, vol. 178, Elsavier Publisher.
Pernarowski, et. al., "Continuous Flow Apparatus . . . " Journ. of the Pharmaceutical Sciences, 1968, pp. 1419-1421, vol. 57.

* cited by examiner

Primary Examiner—Jan M Ludlow
(74) Attorney, Agent, or Firm—Tifani H. Cottingham

(57) ABSTRACT

Equipment and method of use for in vitro buccal dissolution testing. The invention is particularly useful for evaluating the effect of taste-masking in oral dosage forms.

7 Claims, 2 Drawing Sheets

BUCCAL DISSOLUTION OF ACTIVE SUBSTANCES

BACKGROUND OF THE INVENTION

Active substances used in the pharmaceutical industry frequently have an objectionable taste. This presents difficulties in the development of formulations because objectionable taste can lead to poor patient compliance. This problem is particularly severe in liquid, chewable and fast dissolving dosage forms. There are two main techniques known in the art for masking this taste. The first is to add flavors to hide the objectionable taste. The second is to limit the dissolution of the active substance in the saliva.

There are currently no in vitro test methods designed for assessing the taste masking properties of taste-masked formulations. There are a multiplicity of tests available for in vitro testing of dissolution of formulations intended for gastro-intestinal (GI) dissolution (US Pharmacoapeia 24), but none of them are suitable for buccal systems. For the purposes of this discussion such methods will be referred to as GI dissolution methods. Buccal dissolution is characterized by some unique requirements. Firstly, for taste masking, incomplete buccal dissolution is a highly desirable property, whereas a primary aim of all GI dissolution methods is complete dissolution. Secondly, buccal residence times are very short, of the order of several minutes, based on saliva secretion rates. GI residence times are of the order of hours. Thirdly, undissolved components, for example small particles, are removed from the mouth by swallowing so that their residence time is of the order of 5-60 seconds. No current GI dissolution tests make allowance for removal of undissolved components from the test chamber.

Since dissolved compounds can impart a bad taste, there is a need in the art for an in vitro test method that can characterize the dissolution of compounds in the buccal cavity under conditions that are physiologically relevant.

Applicants have invented a test method and apparatus that satisfies this need.

The following terms have the following meanings herein:

The term "release medium" as used herein, means the liquid medium into which the substance is being released. Examples of release media can be simulated saliva, water, and various buffer solutions.

The term 'residence time' as used herein, is a well known engineering concept applied to continuous flow systems, and is calculated by mathematically dividing the volume of liquid in a vessel by the flow rate into an out of the vessel such that the volume of liquid remains constant. For example, a flow rate of 5 ml/min into and out of a vessel containing 10 ml of liquid has a residence time of 2 minutes.

The term 'resinate' as used herein, means the product derived from forming a complex between an ion exchange resins and an ionizable organic compound.

STATEMENT OF THE INVENTION

Figure 1:
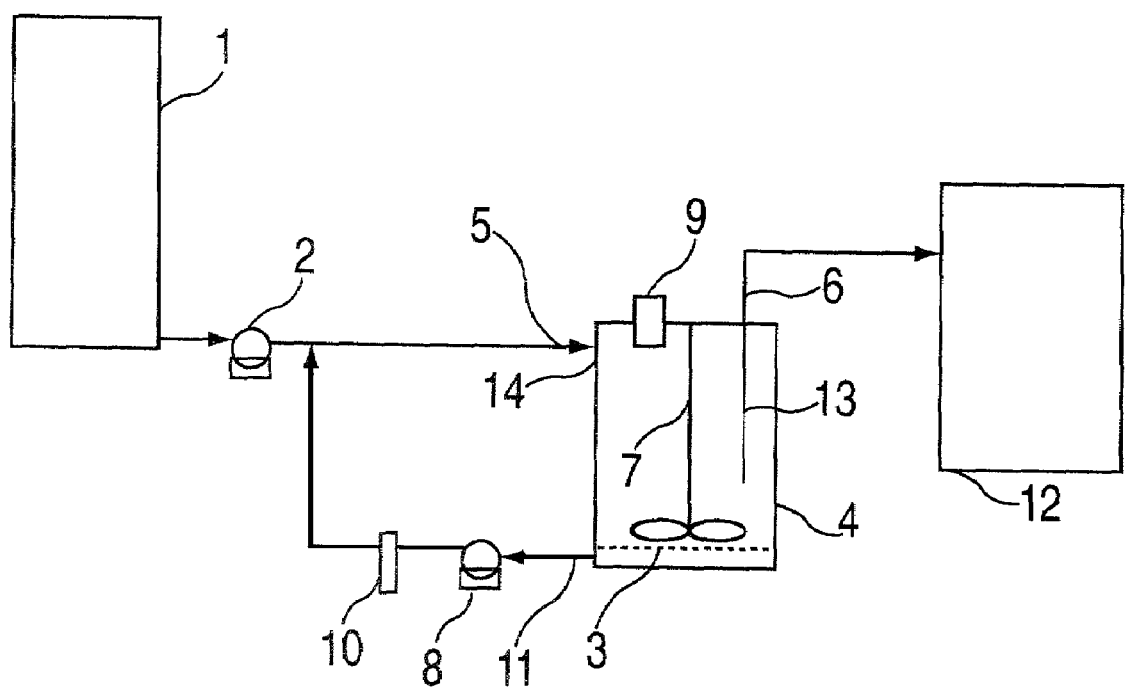
FIG. 1 is a schematic representation of one of the embodiments of the invention.

The present invention relates to an apparatus for conducting buccal dissolution tests comprising:

a) a cell;
b) a supply of a release medium that can be continuously passed into said cell;
c) a means of removing a sample from said cell such that any undissolved solids are not included in said sample;
d) a means of analyzing said sample for substances of interest in the test;
e) a means of controlling the temperature of the release medium in said cells;

wherein said cell is capable of transferring solid particles out of said cell;

wherein said solid particles are of small particle size;

wherein said cell has a means of adding test materials;

wherein said cell has a means of mixing the sample and release medium;

wherein further said means of analyzing the effluent can be carried out at multiple times during the operation of the test equipment.

The present invention further relates to a buccal dissolution test method for use with said apparatus, comprising the steps of:

a) passing a release medium through the cell;
b) adding the test sample to said cell;
c) passing release medium through said cell such that any undissolved portion of the test sample is transferred out of the cell;
d) removing samples of the release medium from the cell, such that they do not contain any undissolved material;
e) maintaining the temperature of said cells at the desired temperature for the duration of the test;
f) analyzing the effluent from said cells to determine the concentration of substance dissolved from the test sample.

Further, the flow rate of release medium and volume of liquid in the cell is constant throughout the test, wherein further the flow rate of release medium, temperature of the release medium, volume of liquid in the cell, and amount of test sample are adjusted to give physiologically relevant conditions.

DETAILED DESCRIPTION OF THE INVENTION

The present invention relates to an apparatus for conducting dissolution tests comprising:

a) a cell;
b) a supply of a release medium that can be continuously passed into said cell;
c) a means of removing a sample from said cell such that any undissolved solids are not included in said sample
d) a means of analyzing said sample for substances of interest in the test;
e) a means of controlling the temperature of the release medium in said cells;

wherein said cell is capable of transferring solid particles out of said cell;

wherein said solid particles are of small particle size;

wherein said cell has a means of adding test materials;

wherein said cell has a means of mixing the sample and release medium;

wherein further said means of analyzing the effluent can be carried out at multiple times during the operation of the test equipment.

The present invention further relates to a buccal dissolution test method for use with said apparatus, comprising the steps of:

g) passing a release medium through the cell;
h) adding the test sample to said cell;
i) passing release medium through said cell such that any undissolved portion of the test sample is transferred out of the cell;
j) removing samples of the release medium from the cell, such that they do not contain any undissolved material;
k) maintaining the temperature of said cells at the desired temperature for the duration of the test;
l) analyzing the effluent from said cells to determine the concentration of substance dissolved from the test sample.

Further, the flow rate of release medium and volume of liquid in the cell is constant throughout the test, wherein further the flow rate of release medium, temperature of the release medium, volume of liquid in the cell, and amount of test sample are adjusted to give physiologically relevant conditions.

According to the present invention, there is provided an apparatus for assessing buccal dissolution of a pharmaceutical composition comprising:

a) a chamber capable of containing a pharmaceutical composition within a medium;
  wherein said chamber comprises:
  i) a housing;
  ii) a mixer
  iii) a first inlet and a first outlet provided on the housing for the supply of a medium to the housing and outflow of medium from the housing; wherein the said first outlet allows small particles of undissolved solid to exit the chamber along with the medium.
  iv) a second outlet provided on the housing for outflow of medium from the housing
  v) a second inlet, herein called the sample port, provided on the housing for the addition of test material
  vi) a filtration device capable of retaining undissolved pharmaceutical composition within the housing, which is permeable to medium and is positioned between the inside of the housing and said second outlet of the medium, such that the medium flowing out of said second inlet is essentially free of solid particles;
  vii) a flow controller of said first medium into the chamber;
b) a medium analysis device in fluid communication with the chamber for determining the dissolution profile of the pharmaceutical composition; whereby the appearance of the pharmaceutically active compound in the medium flowing out of the chamber is analyzed to determine dissolution of the compound.
c) a flow controller provided to shunt the medium flowing out of the said second outlet of the housing, to the inlet of the chamber;
d) heating and insulating devices provided to control the temperature of the medium in the housing.

Further, the flow rate of release medium, temperature of the release medium, volume of liquid in the cell, and amount of test sample are adjusted to give physiologically relevant conditions.

Referring to FIG. 1, in one embodiment, the invention comprises a reservoir (1), a pump (2) and a filtration cell (4) arranged so that liquid in reservoir (1) is transferred to cell (4) via pump (2). The cell (4) comprises a stirrer (7), a filter membrane (3), an inlet (5), an outlet (11), an outlet (6) through which passes a dip-tube (13), a tight fitting lid (14), and a sample addition port (9). The outlet (11) is positioned such that only liquid that has passed though the filter (3) can exit through it. The outlet (11) is connected to a pump (8) and a flow-through uv cell (10), such that the liquid exiting the outlet (11) passes through the uv cell (8) and is returned to the inlet (5) of the cell (4). The dip tube (13) exits the cell (4) through the outlet (6), and connects to the reservoir (12) such that any material that enters the dip-tube (13) is collected in said reservoir. The uv cell (10) is placed in a suitable uv spectrophotometer to allow the measurement of the absorbance of the cell at a desired wavelength. If temperature control is required the cell (4) can be immersed in a suitable heating bath. In one embodiment the sample addition port (9) is a hole with a rubber stopper. In another embodiment it is a metal fitting containing a rubber septum that can be penetrated with a syringe.

In a further embodiment the liquid exiting the outlet (11) passes through the uv cell (10) and is then directed into another reservoir, similar in requirements to the reservoir (12), and is not returned to the cell (4).

In a further embodiment a de-aerator can be installed before the uv cell (10) to remove entrained gas bubbles.

When in use, referring to the embodiment illustrated in FIG. 1, the reservoir (1) is filled with release medium, and the desired volume of release medium is added to the cell (4). The pumps are started and operated until liquid is flowing into the reservoir (12), the uv absorbance indicated by the spectrophotometer is constant, herein called the baseline value, and there are no air bubbles in the lines or the uv cell. The sample to be tested is then added to the cell (4). As the active substance present in said sample is dissolved, the uv absorbance will increase, reach a peak, and then decrease. The test is continued to a suitable endpoint. Examples of such endpoints are, the return of the uv absorbance to the baseline value, or a fixed time such as six times the residence time in cell (4). It is clear to one skilled in the art how to determine which endpoint is most appropriate for the specific sample being tested.

The data collected from the spectrophotometer can be used to calculate the instantaneous concentration of the active substance. The data can be used to characterize the release rate and the total amount of active substance released.

In one embodiment of this invention suitable for testing buccal absorption, part or all of the effluent from the uv cell (10) is passed directly to the reservoir (12). The portion of dissolved active ingredient in said part of the effluent represents the absorption of the active ingredient through the buccal mucosa.

While the present invention uses a heating bath, any heating device can be used to control the temperature of the filtration cells. For testing at ambient temperature the invention can be operated without a heating device.

Dosage forms that can be tested with this invention include, but are not restricted to powders, syrups, adhesive devices, suspensions, tablets that dissolve or disintegrate in the mouth, and lozenges.

The invention is not limited to the use of a uv spectrophotometer as the method of analysis. Any in-line analysis known in the art that is applicable to the active substance and release medium can be used. The invention can also be used by removing samples from the outlet (11) instead of, or in addition to in-line analysis. Filtration cells useful in the invention can be any vessel that provides the requirements of agitation, volume, filtration speed, filtration efficiency, compatibility with the active substance, and compatibility with the release medum. The preferred filtration cells are continuous, stirred filtration cells, such as the Amicon stirred ultrafiltration cell models 8003, 8010, 8050, 8200, and 8400, available from Millipore® Corporation. The most preferred filtration cells are the Amicon® stirred ultrafiltration cell models 8003, 8010, and 8050, available from Millipore® Corporation.

The tubing used in the dip-tube can be any tubing compatible with the release media. The length of said tubing is adjusted such that the lower end is below the surface of the liquid in the filtration cell (4). The cross-sectional diameter of the tubing is selected so that small particles are carried up the tubing by the flow of the release medium and so that particles do not clog the tubing. In practice, the inventors have determined that tubing with an internal diameter of 0.5 to 3.0 mm fulfills these requirements for flow rates to the cell (4) in the range 0.5 to 5 ml/min. For other flow rates other internal diameters may be needed. It is clear to one skilled in the art that suitable internal diameters for the said tube can be selected by trial and error, or by calculation using suitable hydrodynamic considerations.

Release media useful in the practice of the invention can be any fluid of physiological relevence. Preferred fluids are water and simulated saliva. The most preferred fluid is simulated saliva.

The US Pharmacopeia 24 does not make any recommendation for the composition of simulated saliva. There are several publications, (See, Karin M. Höld, Douwe de Boer, Jan Zuidema, and Robert A. A. Maes. 'Saliva as an Analytical Tool in Toxicolgy' Int. J. Drug Testing, 1, 1995. V. W.-H Leung and B. W. Darvell, Journal of Dentistry, 25, 475-484, 1997 and references therein) describing the compositions of saliva. It is clear to one skilled in the art that simulated saliva compositions suitable for the practice of this invention can be selected from these publications. A suitable, non limiting example is as follows:

| | |
|---|---|
| Potassium dihydrogenphosphate | 1.632 g/l |
| Sodium chloride | 2.34 g/l |
| Calcium chloride dihydrate | 0.167 g/l |
| 0.2 M Sodium hydroxide to give pH 6.2 | ~12 g/l |

Flow rates useful in the practice of the invention can be constant throughout the test or changed during the test.

Flow rates and cell volumes useful in the practice of this invention can be selected to give residence times in the filtration cell from 0.1 minutes to 60 minutes. Preferred residence times are 0.5 minutes to 30 minutes. Most preferred residence times are 1 minute to 15 minutes.

The flow rate of the sampling pump (8) depends on whether the sample flow is returned to the cell (4). When the sample flow is returned to the cell the flow must be high enough such that there is a very short residence time in the sample loop. Sample loop residences times useful in the practice of the invention are from 2 seconds to 2 minutes. Preferred sample loop residence times are from 2 seconds to 30 seconds. When the sample flow is not returned to the cell (4) the flow rate of the sample line reduces the flow rate exiting the cell (4) through the dip tube (13). In this case the sample flow should be such that it does not deleteriously affect the removal of undissolved particles through the dip tube. Sample line flow rates in this case are 5% to 50% of the flow rate of the main pump (2), subject to the limitation that the flow through the dip tube must meet the requirements provide above. Preferred flow rates in this case are 10% to 25% of the flow rate of the main pump (2), subject to the limitation that the flow through the dip tube must meet the requirements provide above.

Filter membranes useful in the practice of this invention can be any of the commercially available filter membranes that are compatible with the release media. Preferred filter membranes have a nominal particle size cut-off of not more than 10 microns. The more preferred filters have a nominal particle size cut-off of 0.25-5 microns. The most preferred filter membranes have a nominal particle size cut-off of 1-3 microns.

De-aerators useful in the practice of the invention can be any of the commercially available systems, provided that they do not have a hold-up volume that causes significant broadening of the release profile. Preferred de-aerators useful in the operation of the invention should have a hold-up volume less than half of the filtration cell volume. More preferred de-aerators useful in the operation of the invention should have a hold-up volume less than one quarter of the filtration cell volume. Most preferred de-aerators useful in the operation of the invention should have a hold-up volume less than one tenth of the filtration cell volume.

Flow controllers useful in the practice of the invention include any device capable of producing a flow of the media into and out of the chambers as described above. These include pumps, pressurized systems with control valves, suction systems with control valves and combinations. The preferred flow controllers are pumps, and pressurized systems with control valves, and combinations of them. The pumps useful in the invention can be any pump capable of attaining the desired flow rates and maintaining said flow rates constant throughout the test. These include but are not limited to, general purpose positive displacement pumps, peristaltic pumps, diaphragm pumps, HPLC quality positive displacement pumps, and centrifugal pumps. Preferred pumps useful in the invention are peristaltic pumps, diaphragm pumps, and HPLC quality positive displacement pumps. Most preferred are peristaltic pumps and HPLC quality positive displacement pumps.

Heating devices useful in the practice of the present invention can be any of those known in the art that give sufficiently uniform and accurate temperature control. The preferred heating device will be able to control the temperature to within +/−2° C. of the desired temperature. The more preferred heating device will be able to control the temperature to within +/−1° C. of the desired temperature. The preferred heating device will be able to control the temperature in conformity with the most current recommendations in the US Pharmacopeia and like sources.

Medium analysis devices useful in the practice of the present invention include, but are not limited to, any detector known in the art that generates physical and/or chemical data of a pharmaceutical or active test agent, e.g., the use of a UV spectrophotometer as the method of analysis. In a preferred embodiment, the detector is capable of acquiring data characteristic of a particular agent by any method selected from the group consisting of ultraviolet radiation, infrared radiation, nuclear magnetic resonance, Raman spectroscopy, electrochemical, biosensors, and mixtures thereof. Any in-line detector known in the art that is applicable to the active substance and release medium can be also be used.

The medium analysis device preferably includes a detector operatively associated with the dissolution medium for at least the time period required to reach the end point as described herein-above, and a data processor for continually processing the generated data for the same time period to obtain a dissolution profile of the dosage form. The data processor may be any device capable of continuously processing the data generated by the detector. In a preferred embodiment, the data processor is a computer. The data generated by the detector is preferably stored and/or analyzed by the computer. In a particularly preferred embodiment, the data collector is a computer that has data processing software.

The data is preferably continuously processed by the software as it is received from the detector. In preferred embodiment of the present invention, the detector measures the concentration of the therapeutically active agent in the media surrounding the dosage form. By measuring the concentration of the agent in the surrounding media, the amount of agent release from the dosage form can be calculated.

The invention can also be used by removing samples from the chambers directly or from the effluent discharge of the chambers instead of, or in addition to in-line analysis. In such an embodiment the analytical methods can be any method known in the art, including but not limited to, gas chromatography, liquid chromatography, high performance liquid chromatography (HPLC), colorimetry, uv spectroscopy, IR spectroscopy, Raman spectroscopy, near IR spectroscopy, biosensors, electrochemical methods, mass spectroscopy, and nuclear magnetic spectroscopy. In the most preferred embodiment the medium analysis is performed in-line using uv spectroscopy. It is clear to one skilled in the art that any combination of the medium analysis devices can be used as appropriate for the data required.

It is known to those skilled in the art that the safe and effective operation of flow generating devices, such as pressure feed systems and pumps, requires the inclusion of various other mechanical, electrical and electronic equipment. Said equipment typically includes pressure relief valves, check valves, pressure relief piping, pressure control systems, surge suppressors, surge tanks, mechanical and electronic flow control systems, pressure gauges, and flow gauges.

Further, one skilled in the art will appreciate that the present invention can be adapted for use in determining total gastrointestinal dissolution by the addition of cells that contain fluids such as simulated gastric fluids and simulated intestinal fluid.

The following non limiting examples illustrate the present invention.

EXAMPLE 1

Preparation of Paroxetine/IRP69 Resinate 7.5 g of paroxetine HCl hemidyrate was added to 1492 g of deionized water and stirred vigorously for 5 hours. The solution was filtered and the filtrate analyzed for paroxetine by uv spectrometry to be 4.85 g/l expressed as paroxetine HCl hemihydrate. 163.5 g of the solution was then mixed with 5.5 g of a strongly acid ion exchange resin in the sodium form (AMBERLITE® IRP69 available from Rohm and Haas Company, Philadelphia, Pa.) and shaken overnight. The resinate was isolated by filtration and minimal water washing. The amount of paroxetine loaded onto the resin was 72 mg/g based on the wet resinate.

EXAMPLE 2

Preparation of Paroxetine/IRP64 Resinate

A 5.7 g/l solution of paroxetine was prepared in a manner similar to that in Example 1. 3 g of a weakly acidic ion exchange resin (AMBERLITE® IRP64 available from Rohm and Haas Company, Philadelphia, Pa.) was added to 586 g of the paroxetine solution and shaken overnight. The resinate was isolated by filtration and minimal washing. The amount of paroxetine loaded onto the resin was 10 mg/g based on the wet resinate.

EXAMPLE 3

Release Test on Paroxetine and Paroxetine Resinates

Figure 2:
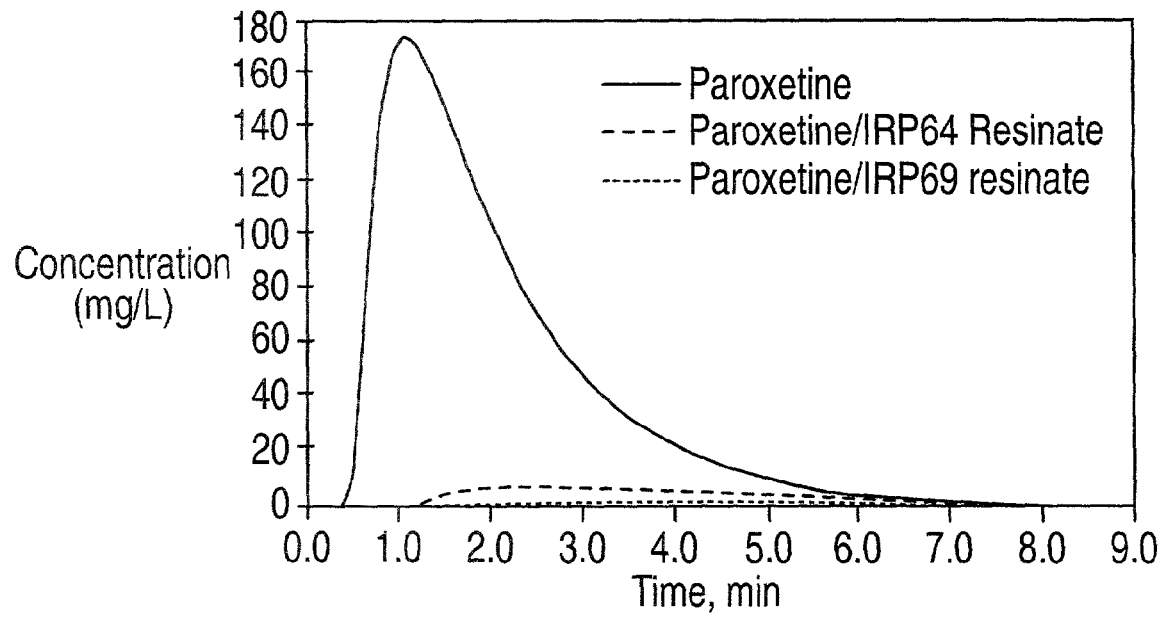
FIG. 2 is graph showing buccal dissolution curves for paroxetine HCl and paroxetine resinates.

A buccal dissolution test was run using paroxetine HCl hemihydrate as a 5% solution, and resinate formulations made as in Examples 1 and 2. The amount of active substance in each test was approximately 10 mg. For these examples the effluent from the uv cell was not returned to the filtration cell. The total flow rate of simulated saliva was 3 ml/min, the flow rate through the uv cell was approximately 1 ml/min and the test was run at room temperature. The dissolution profiles are shown in FIG. 2. This example clearly demonstrates the ability of the method to differentiate the taste masking effect of resinates.

EXAMPLE 5

Release Test on Fast Dissolving Tablets

Figure 3:
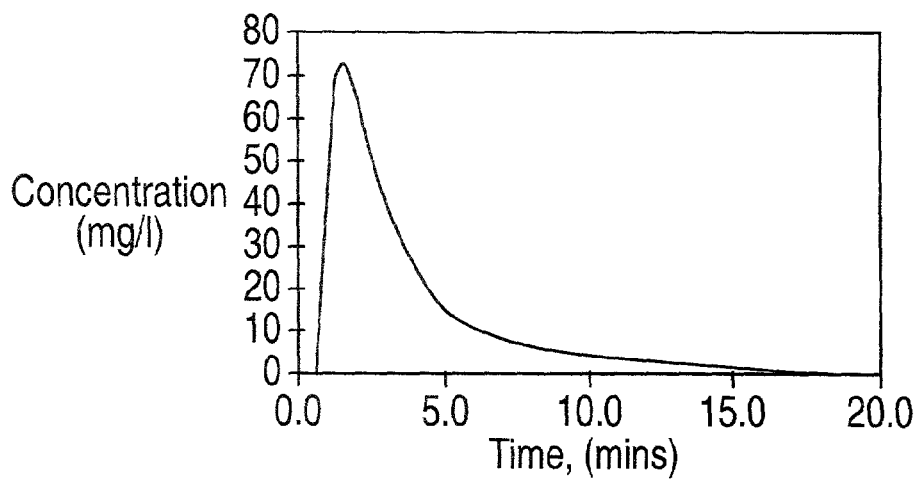
FIG. 3 is graph showing a buccal dissolution curve for a fast dissolving tablet containing loratidine.

A buccal dissolution test was run using a fast-melt tablet formulation of loratidine, containing 10 mg of loratidine. For this example the effluent from the uv cell was not returned to the filtration cell, and a de-aerator was installed immediately before the uv cell (HPLC MP Debubbler available from Kontes Glass Co, New Jersey). The total flow rate of simulated salival fluid was 5.71 ml/min, the flow rate through the uv cell was 2.24 ml/min and the test was run at room temperature. The dissolution profile is shown in FIG. 3 and indicates a peak concentration of 72.7 mg/l of loratidine. This example demonstrates the ability of the method to test fast-melt tablets.

Preparation of Simulated Saliva 750 ml of deionized water and a magnetic stir bar were added to a 1 liter volumetric flask. Then, 1.632 g potassium dihydrogen phosphate, 2.34 g sodium chloride, 0.1665 g of calcium chloride dihydrate and 10 g of 0.2M sodium hydroxide were added with stirring. Deionized water was then added to give a total volume of approximately 950 ml. The mixture was stirred until all the solid was dissolved. 0.2M sodium hydroxide was then added slowly until the pH of the solution was 6.2+/−0.01. The stir bar was removed and the volume made up to the mark with deionized water.

I claim:

1. An in vitro buccal dissolution test method, comprising the steps of:
   a) passing a release medium through a filtration cell, the filtration cell comprising a first chamber separated from a second chamber by a filter, the first chamber having a dip-tube and the second chamber having an outlet separate from the dip-tube, the outlet being connected to a flow-through uv cell;
   b) adding a test sample to the first chamber of the filtration cell;
   c) passing the release medium through the filtration cell such that an undissolved portion of small particles in the test sample is passed through the dip-tube and is transferred out of the filtration cell;
   d) removing samples of the release medium from the filtration cell through the outlet such that the samples of the release medium do not contain any undissolved material;

e) maintaining the temperature of the filtration cell at the desired temperature for the duration of the dissolution test f) performing an in vitro buccal dissolution test by analyzing the samples of the release medium in the flow-through uv cell to determine the concentration of substance dissolved from the test sample;

g) optionally, repeating the step of analyzing the samples of the release medium at multiple times during the duration of the in vitro buccal dissolution test.

2. The in vitro buccal dissolution test method of claim 1, wherein the flow rate of the release medium and volume of liquid in the filtration cell is constant throughout the dissolution test, further provided that the flow rate of the release medium, the temperature of the release medium, the volume of liquid in the filtration cell, and the amount of the test sample are adjusted to give physiologically relevant conditions.

3. The in vitro buccal dissolution test method of claim 1, wherein the release medium is a fluid of physiological relevance.

4. The in vitro buccal dissolution test method of claim 1, wherein the release medium is selected from the group consisting of water, simulated saliva, and buffer solutions.

5. The in vitro buccal dissolution test method of claim 1, wherein the test sample comprises an active substance used in the pharmaceutical industry.

6. The in vitro buccal dissolution test method of claim 1, wherein the test sample has an objectionable taste.

7. The in vitro buccal dissolution test method of claim 1, wherein the dip-tube comprises tubing of internal diameter of 0.5 to 3.0 mm, and wherein the solid particles are carried through the tubing by the flow of the release medium.

* * * * *